US011992580B2

(12) United States Patent
Agerup

(10) Patent No.: US 11,992,580 B2
(45) Date of Patent: *May 28, 2024

(54) METHOD OF SOFT TISSUE AUGMENTATION

(71) Applicant: Palette Life Sciences AB, Solna (SE)

(72) Inventor: Bengt Agerup, Paris (FR)

(73) Assignee: Palette Life Sciences AB, Solna (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/941,713

(22) Filed: Sep. 9, 2022

(65) Prior Publication Data

US 2023/0211051 A1 Jul. 6, 2023

Related U.S. Application Data

(60) Continuation of application No. 16/593,941, filed on Oct. 4, 2019, now Pat. No. 11,458,226, which is a continuation of application No. 15/801,931, filed on Nov. 2, 2017, now abandoned, which is a continuation of application No. 14/169,381, filed on Jan. 31, 2014, now abandoned, which is a division of application No. 11/090,141, filed on Mar. 28, 2005, now abandoned.

(60) Provisional application No. 60/560,258, filed on Apr. 8, 2004.

(51) Int. Cl.
| A61L 27/50 | (2006.01) |
| A61L 15/20 | (2006.01) |
| A61L 15/52 | (2006.01) |
| A61L 15/58 | (2006.01) |
| A61L 27/20 | (2006.01) |
| A61P 43/00 | (2006.01) |

(52) U.S. Cl.
CPC ............... *A61L 27/50* (2013.01); *A61L 15/20* (2013.01); *A61L 15/52* (2013.01); *A61L 15/58* (2013.01); *A61L 27/20* (2013.01)

(58) Field of Classification Search
CPC .......... A61L 27/50; A61L 15/20; A61L 15/52; A61L 15/58; A61L 27/20
See application file for complete search history.

(56) References Cited

U.S. PATENT DOCUMENTS

| 4,642,117 A | 2/1987 | Nguyen et al. |
| 4,657,548 A | 4/1987 | Nichols |
| 4,803,075 A | 2/1989 | Wallace et al. |
| 4,969,901 A | 11/1990 | Binder |
| 5,007,940 A | 4/1991 | Berg |
| 5,399,351 A | 3/1995 | Leshchiner et al. |
| 5,658,592 A | 8/1997 | Tanihara et al. |
| 5,798,096 A | 8/1998 | Pavlyk |
| 5,827,937 A | 10/1998 | Ågerup |
| 5,922,025 A | 7/1999 | Hubbard |
| 6,063,061 A | 5/2000 | Wallace et al. |
| 6,251,876 B1 | 6/2001 | Bellini et al. |
| 6,436,424 B1 | 8/2002 | Vogel et al. |
| 7,637,900 B2 | 12/2009 | Burgess |
| 7,942,930 B2 | 5/2011 | Agerup et al. |
| 8,124,120 B2 | 2/2012 | Sadozai et al. |
| 11,458,226 B2 * | 10/2022 | Ågerup ................... A61P 43/00 |
| 2002/0193448 A1 | 12/2002 | Wallace et al. |
| 2003/0153806 A1 | 8/2003 | Miller |
| 2004/0000103 A1 | 1/2004 | Chen et al. |
| 2004/0267201 A1 | 12/2004 | Agerup |
| 2005/0226936 A1 | 10/2005 | Agerup |
| 2006/0135469 A1 | 6/2006 | Miyata et al. |
| 2010/0028438 A1 | 2/2010 | Lebreton |
| 2014/0147479 A1 | 5/2014 | Agerup |
| 2018/0093017 A1 | 4/2018 | Ågerup |
| 2020/0030494 A1 | 1/2020 | Ågerup |

FOREIGN PATENT DOCUMENTS

| EP | 0402031 A2 | 12/1990 |
| EP | 0 402 031 | 12/1993 |
| EP | 0 730 847 A1 | 9/1996 |
| EP | 0730847 A1 | 9/1996 |
| EP | A 730 847 A1 | 9/1996 |
| EP | 1 552 839 A1 | 7/2005 |
| EP | 1552839 A1 | 7/2005 |
| JP | H824325 A | 1/1996 |
| JP | H0824325 A | 1/1996 |
| JP | 08-508973 A | 9/1996 |
| JP | H08508973 A | 9/1996 |

(Continued)

OTHER PUBLICATIONS

023 Appeal No. T2555/18.3.2.08 Opposition against European Patent No. 1734894 (13 pages).
Abdullah, E. C., A. M. Salam, and A. R. Aziz. "Cohesiveness and flowability properties of silica gel powder." Physics International 1.1 (2010): 16-21. (Year: 2010).
Alazzawi, Mustafa K., et al. "Rheological assessment of cohesive energy density of highly concentrated stereolithography suspensions." Ceramics International 46.6 (2020): 8473-8477. (Year: 2020).
Bourdon et al., "Life Capabilities evaluation of Hyaluronic Acid Fillers," Laboratories Teoxane (2 pages), Jan. 17, 2015.
Bousquet et al.: Restylane Lip Implantation: European Experience. Operative Techniques in Oculoplastic, Orbital and Reconstructive Surgery. 2(4):172-176 (1999).

(Continued)

*Primary Examiner* — Abigail Vanhorn
(74) *Attorney, Agent, or Firm* — WILSON SONSINI GOODRICH & ROSATI

(57) ABSTRACT

Particles made of a viscoelastic medium, are injectable gel particles, and have a size, when subjected to a physiological salt solution, in the range of from 1 to 5 mm. The particles are useful in a soft tissue augmentation implant. The implant includes particles of a viscoelastic medium, wherein a major volume of the particles are injectable gel particles The implant is useful in a method of soft tissue augmentation in a mammal, including man, comprising subepidermal administration at a site in said mammal where soft tissue augmentation is desirable, of an implant.

20 Claims, No Drawings

(56) References Cited

FOREIGN PATENT DOCUMENTS

| | | |
|---|---|---|
| JP | 2000-239147 A | 9/2000 |
| JP | 2000239147 A | 9/2000 |
| JP | 2002-515086 A | 5/2002 |
| JP | 2002515086 A | 5/2002 |
| JP | 2004-181121 | 7/2004 |
| JP | 2004181121 A | 7/2004 |
| RU | 2067873 C1 | 10/1996 |
| WO | WO-85/00969 A | 3/1985 |
| WO | WO-8500969 A1 | 3/1985 |
| WO | WO-86/00079 | 1/1986 |
| WO | WO-8600079 A1 | 1/1986 |
| WO | WO-96/02209 A1 | 2/1996 |
| WO | WO-9602209 A1 | 2/1996 |
| WO | WO-98/08550 A1 | 3/1998 |
| WO | WO-9808550 A1 | 3/1998 |
| WO | WO-99/10021 A | 3/1999 |
| WO | WO-9910021 A1 | 3/1999 |
| WO | WO-01/19287 A1 | 3/2001 |
| WO | WO-0119287 A1 | 3/2001 |
| WO | WO-2004/016275 | 2/2004 |
| WO | WO-2004016275 A1 | 2/2004 |
| WO | WO-2004/069090 A2 | 8/2004 |
| WO | WO-2004069090 A2 | 8/2004 |
| WO | WO-2005097218 A2 | 10/2005 |

OTHER PUBLICATIONS

Carruthers et al.: A prospective, randomized, parallel group study analyzing the effect of BTX-A (Botox) and nonanimal sourced hyaluronic acid (NASHA, Restylane) in combination compared with NASHA (Restylane) alone in severe glabellar rhytides in adult female subjects: treatment of severe glabellar rhytides with a hyaluronic acid derivative compared with the derivative and BTX-A. Dermatol Surg. 29(8):802-809. doi:10.1046/j.1524-4725.2003.29212.x (2003).

Declaration of Dr. Katarina Edsman, (13 pages), Oct. 20, 2017.

Duranti et al.: Injectable hyaluronic acid gel for soft tissue augmentation. A clinical and histological study. Dermatol Surg. 24(12):1317-125. doi:10.1111/j.1524-4725.1998.tb00007.x (1998).

Edsman et al., "Cohesion of Hyaluronic Acid Fillers" Correlation Between Cohesion and Other Physiochemical Properties, ISSN: 1076-0512, Dermatol. Surg., vol. 44, 2018, pp. 557-562.

Evaluating the rheological properties of hyaluronic acid hydrogels for dermal filler applications 024 Appeal No. 12555/18.3.2.08 Opposition against European Patent No. 1734894, Malvern Instruments Limited 2015.

Fallacara et al., "Hyaluronic Acid Fillers in Soft Tissue Regeneration" Publishers, Inc., Facial Plastic Surgery, vol. 33, No. 1, Feb. 2017 (11 pages).

Friedman et al.: Safety data of injectable nonanimal stabilized hyaluronic acid gel for soft tissue augmentation. Dermatol Surg. 28(6):491-494. doi:10.1046/j.1524-4725.2002.01251.x (2002).

Jordan, D. R., "Soft-tissue fillers for wrinkles, folds, and volume augmentation," Can J Ophthalmol, vol. 38, No. 4, 2003, pp. 285-288.

Larsen et al.: Hylan gel biomaterial: dermal and immunologic compatibility. J Biomed Mater Res. 27(9):1129-1134 doi:10.1002/jbm.820270903 (1993).

Macrolane Clinical Guide 1-27, Q-MED AB, Uppsala, Sweden (2009).

Madeline C. Krauss, "Recent Advances in Soft Tissue Augmentation," Seminars in Cutaneous Medicine and Surgery, vol. 18, No. 2, Jun. 1999, pp. 119-128.

Manna, F., et al. "Comparative chemical evaluation of two commercially available derivatives of hyaluronic acid (Hylaform® from rooster combs and Restylane® from *streptococcus*) used for soft tissue augmentation." Journal of the European Academy of Dermatology and Venereology 13.3 (1999): 183-192. (Year: 1999).

Michael Olenius, "The First Clinical Study Using a New Biodegradable Implant for the Treatment of Lips, Wrinkles, and Folds," Aesthetic Plastic Surgery, vol. 22, 1998, pp. 97-101.

Narins et al.: A randomized, double-blind, multicenter comparison of the efficacy and tolerability of Restylane versus Zyplast for the correction of nasolabial folds. Dermatol Surg. 29(6):588-595. doi:10.1046/j.1524-4725.2003.29150.x (2003).

Office Action issued on Australian Patent Application No. 2005231674 dated Feb. 17, 2010.

Office Action issued on Japanese Application No. 2007-507278 dated Jun. 7, 2011.

Office Action issued on JP Application No. 2012-145051 dated Oct. 28, 2014.

Per Heden et al., "Body Shaping and Volume Restoration: The Role of Hyaluronic Acid," Aesth. Plast. Surg. (Mar. 12, 2009).

Perfane "Summary of Safety and Effectivenes Data For a supplemental Premarket Approval Application," Perlane Injectable Gel (16 pages), May 2, 2007.

Pierre et al., "Basics of Dermal Diller Rheology" Original Articles, American Society for Dermatologic Surgery, Inc. published by Wolters Kluwer Health, Inc., 2015, pp. S 120-S 126.

Prada, Pedro J., Transperineal Injection of Hyaluronic Acid in the Anterior Perirectal Fat to Decrease Rectal Toxicity from Radiation Delivered with Low-Dose-Rate Brachytherapy for Prostate Cancer Patients, Brachytherapy, vol. 8, 2009, Elsevier, pp. 210-217.

Response to Office Action dated Feb. 17, 2010 issued on Australian Patent Application No. 2005231674 dated Aug. 20, 2010.

Soft Tissue, Wikipedia, retrieved from: https://en.wikipedia.org/w/index.php?title=Soft tissue&oldid=823283389 (3 pages), Jan. 31, 2018.

"Summary of Safety and Effectivenes Data For a supplemental Premarket Approval Application," Perlane Injectable Gel (16 pages).

Abdullah et al., "Cohesiveness and flowability properties of silica gel powder," Physics International, vol. 1, No. 1, 2010, pp. 16-21.

Alazzawi et al., "Rheological assessment of cohesive energy density of highly concentrated stereolithography suspensions." Ceramics International 46.6 (2020): pp. 8473-8477.

Bourdon et al., "Life Capabilities evaluation of Hyaluronic Acid Fillers," Laboratories Teoxane (2 pages).

Declaration of Dr. Katarina Edsman, Aug. 20, 2010, 13 pages.

Declaration of Dr. Katarina Edsman, Oct. 20, 2017 (13 pages).

Duranti et al., "Injectable Hyaluronic Acid Gel for Soft Tissue Augmentation: A Clinical and Histological Study," Dermatol. Surg., vol. 24, 1998, pp. 1317-1325.

Friedman et al., "Safety Data of Injectable Nonanimal Stabilized Hyaluronic Acid Gel for Soft Tissue Augmentation," Dermatol. Surg., vol. 28, Jun. 2002, pp. 491-494.

Heden et al., "Body Shaping and Volume Restoration: The Role of Hyaluronic Acid," Aesth. Plast. Surg. vol. 44, (pp. 1286-1294).

Krauss, "Recent Advances in Soft Tissue Augmentation," Seminars in Cutaneous Medicine and Surgery, vol. 18, No. 2, Jun. 1999, (13 pages).

Larsen et al., "Hylan Gel Biomaterial: Dermal and Immunologic Compatibility," Journal of Biomedical Materials Research, vol. 27, 1993, (pp. 1129-1134).

Manna et al., "Comparative chemical evaluation of two commercially available derivatives of hyaluronic acid (Hylaform from rooster combs and Restylane from *streptococcus*) used for soft tissue augmentation," Elsevier, Journal of the European Academy of Dermatology and Venereology, vol. 13, 1999, pp. 183-192.

Narins et al., "A Randomized, Double-Blind, Multicenter Comparison of the Efficacy and Tolerability of Restylane Versus Zyplast for the Correction of Nasolabial Folds," Dermatol. Surg., vol. 29, Jun. 2003, (pp. 588-595).

Olenius, "The First Clinical Study Using a New Biodegradable Implant for the Treatment of Lips, Wrinkles, and Folds," Aesthetic Plastic Surgery, vol. 22, 1998, (pp. 97-101).

Response to Office Action dated Feb. 17, 2010 issued on Australian Patent Application No. 2005231674 dated Aug. 20, 2010 (12 pages).

Soft Tissue, Wikipedia, retrieved from: https://en.wikipedia.org/w/index.php?title=Softtissue&oldid=823283389 (3 pages).

Opposition against European Patent No. 1734894 dated May 2, 2017 (15 pages).

PCT/SE2005/000504 International Search Report dated Sep. 27, 2005.

(56) References Cited

OTHER PUBLICATIONS

PCT/SE2005/000504 International Written Opinion dated Sep. 23, 2005.
U.S. Appl. No. 11/090,141 Patent Board Decision on Appeal dated Jun. 14, 2016.

* cited by examiner

METHOD OF SOFT TISSUE AUGMENTATION

CROSS REFERENCE TO RELATED APPLICATIONS

This application is a continuation of U.S. application Ser. No. 16/593,941, filed on Oct. 4, 2019, which is a continuation of U.S. application Ser. No. 15/801,931, filed on Nov. 2, 2017, which is a continuation of U.S. application Ser. No. 14/169,381, filed on Jan. 31, 2014, which is a division of U.S. application Ser. No. 11/090,141 filed on Mar. 28, 2005, which claims the benefit under 35 U.S.C. § 119(e) of U.S. Provisional Patent Application No. 60/560,258, filed Apr. 8, 2004. The entire contents of each of U.S. application Ser. No. 15/801,931, U.S. application Ser. No. 14/169,381, U.S. application Ser. No. 11/090,141, and U.S. Provisional Patent Application No. 60/560,258 are hereby incorporated herein by reference in their entirety.

FIELD OF THE INVENTION

The present invention relates to the fields of esthetics and plastic surgery, including cosmetic and reconstructive surgery. More specifically, the invention is concerned with a method of soft tissue augmentation in a mammal, including man. Moreover, the invention is directed to use of particles of a viscoelastic medium for the manufacture of a medicament for therapeutic soft tissue augmentation in a mammal, including man. The invention is also concerned with particles of a viscoelastic medium, production thereof, and use thereof in an implant.

BACKGROUND TO THE INVENTION

An implant material that is useful for soft-tissue augmentation should ideally be capable of providing adequate and sustained aesthetic and/or therapeutic correction without migration and displacement; natural-looking and non-palpable; easy to administer and, if necessary, remove; non-immunogenic; and devoid of chronic inflammatory reactions (Krauss M C, Semin Cutan Med Surg 1999; 18: 119-128). As a soft-tissue augmentation material, hyaluronic acid (a naturally occurring polysaccharide) has low immunogenic potential, being chemically homogenous across all species and tissues (Larsen N E et al., J Biomed Mater Res 1993; 27: 1129-1134). Stabilization (or cross-linking) of the hyaluronic acid molecule improves its resistance to enzymatic degradation without compromising its biocompatibility, while the use of a non-animal source reduces the likelihood of antigenic contamination and subsequent hypersensitivity reactions (Friedman et al., Dermatol Surg 2002; 28: 491-4).

Non-animal stabilized hyaluronic acid (NASHA), U.S. Pat. No. 5,827,937, may be produced from a highly purified hyaluronic acid preparation obtained by bacterial fermentation. Various NASHA preparations of different particle size (Restylane® Perlane, Restylane®, Restylane® Fine Lines and Restylane® Touch, all from Q-Med AB, Uppsala, Sweden) have been developed as dermal fillers for facial soft-tissue augmentation. Clinical studies indicate that known NASHA gels are effective in augmenting lips (Bousquet M-T and Ågerup B, Oper Techniques Oculoplast Orbit Reconstruct Surg 1999; 2: 172-176) and correcting facial wrinkles and folds (Olenius M. Aesth Plast Surg 1998; 22: 97-101; Duranti F et al., Dermatol Surg 1998; 24:1317-25; Narins R S et al., Dermatol Surg 2003; 29: 588-95; Carruthers J and Carruthers A, Dermatol Surg 2003; 29: 802-9), and that they offer a more durable aesthetic improvement than bovine collagen or hylan B. The extensive clinical experience gained from their intradermal use in some 1.5 million facial cosmetic procedures confirms their safety.

It is recommended that RESTYLANE Touch (~500,000 particles/ml, mean particle size 0.2 mm) should be injected in the upper part of the dermis; RESTYLANE (~100,000 particles/ml, mean particle size approximately 0.4 mm) should be injected in the mid-part of the dermis; and RESTYLANE Perlane (~10,000 particles/ml, mean particle size approximately 0.8 mm) should be injected in the deep layer of the dermis and/or the surface layer of the subcutis.

Some known soft-tissue augmentation treatments involving implantation of viscoelastic materials occasionally suffer from the drawback that the implant, or part thereof, migrates away from the desired site of treatment. Another problem with some known tissue augmentation treatments involving implantation of viscoelastic materials is that the implant is displaced from the desired site of treatment. Implant migration and displacement are disadvantageous for the patient, since they may impair the cosmetic and/or therapeutic outcome of the treatment and may impede removal of the implant, if this is desired.

SUMMARY OF THE INVENTION

It is an object of the present invention to provide an implantation material suitable for soft tissue augmentation which overcomes drawbacks with known implantation materials. It is also an object of the present invention to provide a method of producing such an implantation material.

It is another object to provide an implant suitable for soft tissue augmentation comprising such an implantation material which overcomes drawbacks with known implants. It is a further object of the present invention to provide an implant suitable for soft tissue augmentation comprising such an implantation material which is readily removable if desired.

It is another object of the present invention to provide a method of soft tissue augmentation in a mammal, including man, which overcomes drawbacks with known methods. It is one object of the present invention to provide a method of soft tissue augmentation in a mammal, including man, comprising subepidermal administration of an implant, which avoids or diminishes undesired migration of the implant from the desired site of implantation. It is one object of the present invention to provide a method of soft tissue augmentation in a mammal, including man, comprising subepidermal administration of an implant, which avoids or diminishes displacement of the implant from the desired site of implantation.

It is also an object of the present invention to provide use of a viscoelastic medium for the manufacture of a medicament for therapeutic soft tissue augmentation in a mammal, including man.

For these and other objects that will be evident from the following disclosure, the present invention provides particles of a viscoelastic medium, which are injectable gel particles having a size, when subjected to a physiological salt solution, in the range of from 1 to 5 mm.

The invention is based on the finding that subepidermal administration of an implant comprising gel particles made of a viscoelastic medium which are considerably larger than previously used in implants made of viscoelastic media are useful in avoiding migration and/or displacement of the implant, or part thereof, from the desired site of soft tissue augmentation. Moreover, the limited displacement of the implant in combination with the considerable particle size facilitates easy removal of the implant, if desired.

In certain preferred particles according to the invention, said size is in the range of from 1 to 2.5 mm. In other preferred particles according to the invention, said size is in the range of from 2.5 to 5 mm.

In preferred particles according the invention, said viscoelastic medium is selected from the group consisting of polysaccharides and derivatives thereof. In more preferred particles according the invention, said viscoelastic medium is selected from stabilized glycosaminoglycans and derivatives thereof. In certain preferred particles according the invention, said viscoelastic medium is selected from the group consisting of stabilized hyaluronic acid, stabilized chondroitin sulfate, stabilized heparin, and derivatives thereof.

In preferred particles according the invention, said viscoelastic medium is selected from the group consisting of cross-linked hyaluronic acid and derivatives thereof. In particularly preferred particles according the invention, the concentration of said viscoelastic medium in said gel particles, when subjected to a physiological salt solution, is in the range of from 5 to 100 mg/ml.

Preferred particles according to the invention are injectable through a 20 gauge or larger needle by application of a pressure of 15-50 N.

According to another aspect of the invention, there is provided a method of producing injectable gel particles of a viscoelastic medium, comprising the steps of: (i) manufacturing a gel with a desired concentration of said viscoelastic medium; and (ii) mechanically disrupting said gel into gel particles having a size, when subjected to a physiological salt solution, in the range of from 1 to 5 mm.

According yet another aspect of the invention, there is provided a soft tissue augmentation implant comprising particles of a viscoelastic medium, wherein a major volume of said particles are injectable gel particles having a size, when subjected to a physiological salt solution, in the range of from 1 to 5 mm. In preferred embodiments of the implant, said size is in the range of from 1 to 2.5 mm. In other preferred embodiments of the implant, said size is in the range of from 2.5 to 5 mm.

According to one aspect of the invention, there is provided a method of soft tissue augmentation in a mammal, including man, comprising subepidermal administration at a site in said mammal where soft tissue augmentation is desirable, of an implant comprising injectable gel particles of a viscoelastic medium, a major volume of said particles having a size, when subjected to a physiological salt solution, in the range of from 1 to 5 mm. In preferred embodiments of the method according to the invention, said administration is selected from the group consisting of subcutaneous administration, submuscular administration and supraperiostal administration.

In certain methods according to the invention, said size is in the range of from 1 to 2.5 mm. In a preferred embodiment of this method, said site of soft tissue augmentation is selected from facial tissue and other tissues covered by exposed skin. In other methods according to the invention, said size is in the range of from 2.5 to 5 mm.

In preferred methods according to the invention, said administration is a selected from the group consisting of single administration and multiple-layer administration.

According to another aspect of the invention, there is provided injectable gel particles according to the invention for use as a medicament. There is also provided an injectable soft tissue augmentation implant comprising injectable gel particles according to the invention for use as a medicament.

According to yet another aspect of the invention, there is provided use of injectable gel particles of a viscoelastic medium according to the invention, a major volume of said particles having an average size, when subjected to a physiological salt solution, in the range of from 1 to 5 mm, for the manufacture of a medicament for therapeutic soft tissue augmentation in a mammal, including man, wherein said medicament is suitable for subepidermal administration according to the invention at a site in said mammal where therapeutic soft tissue augmentation is desirable.

DETAILED DESCRIPTION OF THE INVENTION

According to one aspect of the invention, there is provided particles of a viscoelastic medium, which are injectable gel particles having a size, when subjected to a physiological salt solution, in the range of from 1 to 5 mm. The particles are useful in a soft tissue augmentation implant comprising particles of a viscoelastic medium, wherein a major volume of said particles are injectable gel particles according to the invention, said gel particles having a size, when subjected to a physiological salt solution, in the range of from 1 to 5 mm. The implant, in turn, is useful in a method of soft tissue augmentation in a mammal, including man, comprising subepidermal administration at a site in said mammal where soft tissue augmentation is desirable, of an implant comprising injectable gel particles of a viscoelastic medium, a major volume of said particles having a size, when subjected to a physiological salt solution, in the range of from 1 to 5 mm.

The term "soft tissue augmentation", as used herein, refers to any type of volume augmentation of soft tissues, including, but not limited to, facial contouring (e.g. more pronounced cheeks or chin), correction of concave deformities (e.g. post-traumatic, HIV associated lipoatrophy) and correction of deep age-related facial folds. Thus, soft tissue augmentation may be used solely for cosmetic purposes or for medical purposes, such as following trauma or degenerative disease.

The term "soft tissue", as used herein, refers to tissues that connect, support, or surround other structures and organs of the body. Soft tissue includes muscles, fibrous tissues and fat.

The method according to the invention may be performed in any mammal, including man. It is preferred that that the method is performed in a human subject.

The terms "subepidermal administration" or "subcuticular administration", as used herein, refer to administration beneath the epidermis of the skin, including administration into the dermis, subcutis or deeper, such as submuscularly or into the periosteum where applicable (in the vicinity of bone tissue.

Administration may be performed in any suitable way, such as via injection from standard cannulae and needles of appropriate sizes. The administration is performed where the soft tissue augmentation is desired, such as the chin, cheeks or elsewhere in the face or body.

The term "implant", as used herein, refers widely to any type of implanted or implantable foreign object or material. Implants also include objects or materials that are nearly identical to non-foreign objects or materials. The implant according to the invention is not limited to any particular shape. The final shape of the implant in the body is decided by the skilled man from the purpose of the treatment.

By the term "viscoelastic medium", as used herein, is meant a medium that exhibits a combination of viscous and elastic properties. Specifically, the viscoelastic medium according to the invention is injectable through a 20 gauge or larger needle, such as a 10-20 gauge needle, by application of a pressure of 15-50 N. In particular, the medium, or an implant or a medicament comprising the medium, is suitable for subepidermal injection into a human in need thereof at a desired site.

Viscoelastic media according to the invention include gels, dispersions, solutions, suspensions, slurries and mixtures thereof. It is preferred that the medium is present as a dispersion of gel or gel-like particles. In a preferred embodiment, the implant according to the invention consists of 1-5 mm large particles of one or more viscoelastic media dispersed in a physiological salt buffer or a suitable physiological salt solvent. In another preferred embodiment, the implant further comprises other suitable additives, such as local anesthetics, anti-inflammatory drugs, antibiotics and other suitable supportive medications, e.g. bone growth factors or cells. Optionally, there may also be included a viscoelastic medium, which may be the same or different, which is not present as particles or as particles of a size smaller than 0.1 mm.

It goes without saying that the size of the gel particles according to the invention is dependent upon the ionic strength of the buffer, solution or carrier that is included in and/or surrounding the gel particles. Throughout this specification, given particle sizes assume physiological conditions, particularly isotonic conditions. It shall be noted that, while it is preferred that the gel particles contain and are dispersed in a physiological salt solution, it is contemplated that the gel particles according to the invention can temporarily be brought to different sizes by subjecting the gel particles to a solution of another tonicity. Particles that are within the scope of this invention exhibit a particle size within the given ranges under physiological conditions, e.g. when implanted subepidermally in the body or when subjected to a physiological, or isotonic, salt solution, i.e. a solution with the same tonicity as the relevant biological fluids, e.g. isoosmotic with serum.

Thus, the viscoelastic medium according to the invention is present at least as gel particles or gel-like particles. A major volume, or more than 50% (v/v), of the particles have a size of at least 1 mm, preferably in the range of 1-5 mm in the presence of a physiological salt solution. In preferred embodiments, more than 70% (v/v), preferably more than 90% (v/v), of the particles are within the given size limits under physiological conditions.

As used herein, a physiological, or isotonic, solution is a solution having an osmolarity in the range of 200-400 mOsm/l, preferably 250-350 mOsm/l, more preferably approximately 300 mOsm/l. For practical purposes, this osmolarity is easily achieved by preparation of a 0.9% (0.154 M) NaCl solution.

A suitable way of obtaining a desired particle size involves producing a gel made of a viscoelastic medium at a desired concentration and subjecting the gel to physical disruption, such as mincing, mashing or allowing the gel to pass through a filter with suitable pore size. The resulting gel particles are dispersed in a physiological salt solution, resulting in a gel dispersion or slurry with particles of desired size.

Another aspect of the invention is the density, or hardness, of the gel particles. The gel particle density can readily be regulated by adjustment e.g. of the concentration of the viscoelastic medium and the amount and type of cross-linking agent, if any. Thus, harder particles can be achieved by a higher concentration of the viscoelastic medium in the gel, and thereby in the resulting gel particles. Harder particles are generally less viscoelastic and have a longer half-life in vivo than softer particles. For use in the present invention, it is critical that the particles retain enough viscoelastic properties so that they are still injectable.

In a preferred embodiment of the invention, the implant is a two-component composition, consisting of softer gel particles mixed with harder gel particles. The gel particles may be made of the same or different viscoelastic media. The resulting mixture of gel particles combines desirable properties of softness/hardness for use in soft tissue augmentation and long durability in vivo.

Administration of the implant employing the method according to the invention prevents or diminishes migration and/or displacement of the implant, which comprises or consists of the 1-5 mm large particles under physiological conditions. A further advantage of the invention is that the large size of the particles in combination with the prevented or diminished migration facilitate easy removal of the implant comprising the particles, should it be desired for some reason.

In a preferred embodiment of the invention, the particles have a size in the range of from 1 to 2.5 mm, such as from 1.5 to 2 mm, in the presence of a physiological salt solution. These particles are suitable for administration to subcutaneous, submuscular or supraperiostal tissue. In particular, they are suitable for administration to tissues covered by skin that is exposed in public, such as facial tissue, since the particles and needles that are suitable for this particle size range are not likely to cause bruises or other discolorations. In a preferred embodiment, these particles are administered to deep subcutaneous or to submuscular/supraperiostal tissue, optionally in more than one layer. Deep subcutaneous or submuscular/supraperiostal administration further prevents or diminishes migration of the particles away from the desired site. According to this embodiment, a major volume, or more than 50% (v/v), preferably more than 70% (v/v), more preferably more than 90% (v/v), of the particles are within the given size limits under physiological conditions.

In another embodiment of the invention, the particles have a size in the range of from 2.5 to 5 mm, such as from 3 to 4 mm, in the presence of a physiological salt solution. Implants comprising such particles further prevents or diminishes migration of the particles away from the desired site. According to this embodiment, a major volume, or more than 50% (v/v), preferably more than 70% (v/v), more preferably more than 90% (v/v), of the particles are within the given size limits under physiological conditions.

Particle size may be determined in any suitable way, such as by laser diffraction, microscopy, filtration, etc, and is decided by the longest distance between two ends of the particle. The specific shape of the gel particles is not critical. For spherical particles, the diameter equals the size for this purpose. The size range may be regulated by mechanical disruption, such as mincing, mashing, filtration, etc, of a gel of a suitable concentration of the desired viscoelastic medium.

Viscoelastic media according to the invention include, without being limited thereto, polysaccharides and derivatives thereof. Suitable viscoelastic media include stabilized starch and derivatives thereof. Suitable viscoelastic media can also be selected from stabilized glycosaminoglycans and derivatives thereof, such as stabilized hyaluronic acid, stabilized chondroitin sulfate, stabilized heparin, and derivatives thereof. Suitable viscoelastic media also include stabilized dextran and derivatives thereof, such as dextranomer. The viscoelastic medium may also be a combination of two or more suitable viscoelastic media.

By the term "stabilized", as used herein, is meant any form of chemical stabilization that, under physiological conditions, renders the stabilized compound more stable to biodegradation that the parent compound. Without being limited thereto, stabilized compounds include cross-linked compounds and partially cross-linked compounds.

By the term "derivative" of a polysaccharide, as used herein, is meant any suitable derivative thereof, including cross-linked polysaccharides and substituted polysaccharides, such as sulfated polysaccharides.

Viscoelastic media according to the invention are biocompatible, sterile and present as particles that are readily injectable through standard needles used in medicine, such as 20 gauge or larger needles, preferably 10-20 gauge needles. It is preferable that the viscoelastic medium is of non-animal origin. Advantageously, the media according to the invention are stable, but not permanent, under physiological conditions. According to an embodiment of the invention, at least 70%, preferably at least 90%, of the viscoelastic medium remains for at least two weeks in vivo, more preferably between two weeks and two years. The viscoelastic medium according to the invention is preferably degraded after five years or more in vivo. The term "degraded" implies that less than 20%, preferably less than 10%, of the medium remains in the body.

The viscoelastic medium according to the invention is more resistant to biodegradation in vivo than natural hyaluronic acid. The prolonged presence of the stable viscoelastic substance is advantageous for the patient, since the time between treatments is increased.

A preferable viscoelastic medium according to the invention is cross-linked hyaluronic acid and derivatives thereof. One type of suitable cross-linked hyaluronic acid is obtainable by cross-linking of hyaluronic acid, optionally non-animal, using the method of U.S. Pat. No. 5,827,937.

In brief, said method involves forming an aqueous solution of a water soluble, cross-linkable polysaccharide; initiating a cross-linking of the polysaccharide in the presence of a polyfunctional cross-linking agent; sterically hindering the cross-linking reaction from terminating before gelation occurs, whereby an activated polysaccharide is obtained; and reintroducing sterically unhindered conditions for the activated polysaccharide so as to continue the cross-linking thereof up to a viscoelastic gel.

The cross-linking agent to be used in connection with this particular method is any previously known cross-linking agent useful in connection with polysaccharides, consideration being taken to ensure that the biocompatibility prerequisites are fulfilled. Preferably, however, the cross-linking agent is selected from the group consisting of aldehydes, epoxides, polyaziridyl compounds, glycidyl ethers and divinylsulfones. Of these, glycidyl ethers represent an especially preferred group, of which 1,4-butanediol diglycidyl ether can be referred to as a preferred example.

In this particular method, the initial cross-linking reaction in the presence of a polyfunctional cross-linking agent can be performed at varying pH values, primarily depending on whether ether or ester reactions should be promoted.

An example of a preferred viscoelastic medium is non-animal stabilized hyaluronic acid, commercially available from Q-Med AB, Uppsala, Sweden.

When the injectable medium is a hyaluronic acid medium, the hyaluronic acid concentration is 5 mg/ml or higher. It is preferred that the hyaluronic acid concentration is in the range of 5-100 mg/ml, more preferred 10-50 mg/ml, such as approximately 20 mg/ml.

The cross-linked hyaluronic acid is present as particles or beads of any form. According to this embodiment, a major volume, or more than 50% (v/v), preferably more than 70% (v/v), more preferably more than 90% (v/v), of the particles are at least 1 mm in size, preferably in the range of 1-5 mm. As outlined above, a preferred embodiment involves particles in the range of 1-2.5 mm, preferably 1.5-2 mm. Another preferred embodiment involves particles in the range of 2.5-5 mm, preferably 3-4 mm.

A suitable way of obtaining a desired particle size involves producing a gel made of cross-linked hyaluronic acid at a desired concentration and subjecting the gel to physical disruption, such as mincing, mashing or allowing the gel to pass through a filter with suitable particle size. The resulting gel particles are dispersed in a physiological salt solution, resulting in a gel dispersion or slurry with particles of desired size.

Another aspect of the invention is the density, or hardness, of the particles. Using the manufacturing method of the invention, the cross-linked hyaluronic acid particle density can readily be regulated by adjustment of the concentration of the viscoelastic medium and the amount and type of cross-linking agent. Thus, harder particles can be achieved by a higher concentration of the viscoelastic medium in the gel, and thereby in the resulting gel particles. Harder particles are generally less viscoelastic and have a longer half-life in vivo than softer particles. Useful hyaluronic acid concentrations yielding gel particles of varying hardness are e.g. 20, 25, 40, 50 and 100 mg/ml. For use in the present invention, it is critical that the particles retain enough viscoelastic properties so that they are still injectable as discussed above.

In a preferred embodiment of the invention, softer gel particles, e.g. 15-22 mg/ml cross-linked hyaluronic acid, are mixed with harder gel particles, e.g. 22-30 mg/ml cross-linked hyaluronic acid. The resulting mixture of gel particles combines desirable properties of softness/hardness for use in soft tissue augmentation and long durability in vivo.

According to the invention, the viscoelastic medium is administered, preferably injected, under the epidermis in any suitable way. By way of example, a dermal incision can be made with a scalpel or a sharp injection needle to facilitate transdermal insertion of a larger cannula for administration of the implant according to the invention at the desired site. It is preferred that the administration is performed subcutaneously, submuscularly or supraperiostally.

The implant, consisting of particles of a viscoelastic medium and optionally other suitable ingredients, may be administered as a single aliquot or as layers of multiple aliquots. Optionally, the viscoelastic medium may be replaced, refilled or replenished by a subsequent injection of the same or another viscoelastic medium. The injected volume is determined by the desired augmentation. In a typical tissue augmentation, a volume in the range of 1-500 ml is injected, depending on the purpose and the treated tissue.

According to another aspect of the invention, there is provided a novel use of particles of a viscoelastic medium according to the invention, a major volume of said particles having an average size in the range of from 1 to 5 mm, for the manufacture of a medicament for therapeutic soft tissue augmentation in a mammal, including man, wherein said medicament is suitable for subepidermal administration according to the invention at a site in said mammal where therapeutic soft tissue augmentation is desirable.

According to this aspect, it is preferred that the administration is performed subcutaneously, submuscularly or supraperiostally. The discussion hereinabove regarding suitable particle sizes applies also for this aspect of the invention.

As used herein, the term "therapeutic" involves any kind of preventive, alleviating or curative treatment. Without being limited thereto, this aspect of the invention encompasses that the medicament is for reconstructive augmentation resulting from a medical condition and is part of a medical treatment of the condition. Thus, the therapeutic use is distinguishable from the non-medical, or cosmetic, use in that they are directed to different patient groups. Specifically, the therapeutic use is solely directed to patients in need of reconstructive augmentation resulting from a medical condition and constitutes a part of a medical treatment of this condition in these patients.

Without being limited thereto, the present invention will in the following be further illustrated by way of examples.

EXAMPLES

Example 1 Preparation of Gel Particles of Non-Animal Stabilized Hyaluronic Acid

As previously exemplified in e.g. U.S. Pat. No. 5,827,937, 10 g of hyaluronic acid prepared by fermentation of *Streptococcus* was dissolved in 100 ml of 1% NaOH, pH>9. Cross-linking agent in the form of 1,4-butanediol diglycidyl ether was added to a concentration of 0.2%. The solution was incubated at 40° C. for 4 h.

The incubated solution was diluted with an acidic water solution to reach neutral pH under mixing, yielding a final hyaluronic acid concentration of 20 mg/ml, and again incubated for 12 h at 70° C. The viscoelastic slurry that resulted from this second incubation was then cooled to room temperature and mashed to its final particle size, approximately 1.5-2 mm.

Example 2 Cheek and Chin Augmentation

Materials

A clear, colorless, viscoelastic gel consisting of non-animal stabilized hyaluronic acid (20 mg/ml) dispersed in physiological saline solution. The gel is obtainable e.g. by the method of example 1. The sterilized study material (2 ml) was supplied in a 3 ml glass syringe and was injected subcutaneously and/or supraperiostally using a sterilized 16G×7 or 9 cm Coleman infiltration cannula with a blunt tip (Byron Medical Inc., Tucson, Arizona, USA).

Patient Selection and Study Design

Adult outpatients (>18 years of age) of either gender seeking cheek and/or chin augmentation therapy for aesthetic purposes. For study inclusion, patients were required to agree to abstain from other cosmetic procedures (e.g., further augmentation therapy, botulinum toxin injections, laser or chemical skin resurfacing or facelift procedures) for the duration of the study. Patients who had undergone facial tissue augmentation therapy or laser/chemical peeling procedures within the previous 6 months or aesthetic facial surgery within the previous 12 months were excluded from the study, In addition, patients presenting with active skin disease or inflammation affecting the intended treatment area, those with known allergy/hypersensitivity to local anaesthetics or previous adverse reactions to NASHA, and those currently taking anticoagulant or antiplatelet drugs were excluded from participation. The use of anticoagulants, aspirin and non-steroidal anti-inflammatory drugs was prohibited until the injection site had completely healed.

Injection Technique

The treatment area was cleaned with an antiseptic solution and, if local anaesthesia was required, lidocaine (0.5 or 1.0%)/adrenaline solution was injected at the planned incision site. Additional anaesthesia was provided, if required, by regional nerve block or subcutaneous injection of lidocaine/adrenaline at the proposed implantation site. A dermal incision 1-2 mm in length was made with a scalpel (11 blade) or sharp injection needle to facilitate transdermal insertion of a 16G blunt-tipped cannula for administration of the gel into the subcutaneous, submuscular or supraperiostal adipose tissue. The gel was injected in small aliquots throughout the area requiring augmentation, rather than as a single bolus, by manipulating the cannula into a different tract after each injection, using a tunnelling technique. A maximum of 10 ml (5 syringes) of gel was administered at each treatment session to a maximum of 3 separate anatomical sites (chin and both cheeks). On completion of the injection, the treatment area was massaged to conform to the contour of the surrounding tissue and, if necessary, ice was applied briefly to reduce any swelling.

Satisfactory cheek and/or chin augmentation for at least 3 months was obtained by the method. In particular, deep subcutaneous injection and supraperiostal injection further prevented migration of the implant.

Example 3 Preparation of Gel Particles of Non-Animal Stabilized Hyaluronic Acid with Longer Duration Ten grams of hyaluronic acid prepared by fermentation of *Streptococcus* was dissolved in 100 ml of 1% NaOH, pH>9. Cross-linking agent in the form of 1,4-butanediol diglycidyl ether was added to a concentration of 0.2%. The solution was incubated at 40° C. for 4 h.

The alkaline gel was divided in two portions, which were individually diluted with an acidic water solution to reach neutral pH under mixing, yielding final hyaluronic acid concentrations of 20 mg/ml and 25 mg/ml, respectively. The gels were incubated for 12 h at 70° C. and cooled to room temperature. The two gel portions were combined and mashed to the final particle size, approximately 3-4 mm.

Example 4 Breast Tissue Augmentation

Women with small breasts were injected with a gel obtainable e.g. by the method of example 3. Each breast received 100 ml gel implanted under the glandular region, just on the pectoralis muscle, using a blunt 12 G needle in small aliquots. Care was taken not to disturb the natural tissue. Twelve months following implantation, the breasts were still in good shape with thin nodular implants. The implant did not blur the analysis of mammography.

One woman had changed her mind about having gels in her breasts and requested for removal of the implant. A blunt cannulae (12 G) was used to suck back the gel. Almost all of the implant was aspirated as a clear transparent gel fluid. Analysis showed that the gel maintained its volume but was slightly lower in concentration as compared to the initial concentration (75% of initial), indicating an implant duration of about 2-3 years.

The invention claimed is:

1. A composition comprising particles of a viscoelastic medium comprising stabilized hyaluronic acid,
   wherein said particles are injectable gel particles suitable for implantation having a size,
   when subjected to a physiological salt solution, in the range of from 1.5 to 5 mm, wherein said physiological salt solution has the same osmolarity as a 0.154 M NaCl solution;
   wherein said viscoelastic medium comprises cross-linked hyaluronic acid.

2. The composition of claim 1, wherein said size is in the range of from 1.5 to 2.5 mm.

3. The composition of claim 1, wherein said size is in the range of from 2.5 to 5 mm.

4. The composition of claim 1, wherein the concentration of said viscoelastic medium in said particles, when subjected to said physiological salt solution, is in the range of from 5 to 100 mg/ml.

5. The composition of claim 1, wherein the particles are injectable through a 20 gauge or larger needle by application of a pressure of 15-50 N.

6. The composition of claim 1 wherein the hyaluronic acid is cross-linked with 1,4-butanediol diglycidyl ether.

7. A soft tissue augmentation implant comprising particles of a viscoelastic medium comprising stabilized hyaluronic acid,
   wherein a major volume of said particles are injectable gel particles having a size, when
   subjected to a physiological salt solution, in the range of from 1.5 to 5 mm;
   wherein said viscoelastic medium is selected from the group consisting of cross-linked hyaluronic acid;
   wherein said physiological salt solution has the same osmolarity as a 0.154 M NaCl solution.

8. The soft tissue augmentation implant of claim 7, wherein said size is in the range of from 1.5 to 2.5 mm.

9. The soft tissue augmentation implant of claim 7, wherein said size is in the range of from 2.5 to 5 mm.

10. The composition of claim 1, wherein the composition is formulated for use as a medicament.

11. An injectable soft tissue augmentation implant comprising injectable gel particles of claim 1 for use as a medicament.

12. A method of soft tissue augmentation in a mammal, comprising sub-epidermally administering the composition of claim 1 at a site in said mammal.

13. The method of claim 12, wherein said administering is subcutaneous administration.

14. The method of claim 12, wherein said administering is submuscular administration.

15. The method of claim 12, wherein said administering is supraperiostal administration.

16. The method of claim 12, wherein said size is in the range of from 1.5 to 2.5 mm.

17. The method of claim 12, wherein said size is in the range of from 2.5 to 5 mm.

18. The method of claim 12, wherein said site of soft tissue augmentation is selected from facial tissue and other tissues covered by exposed skin.

19. The method of claim 12, wherein said administering is a single administration.

20. A method of diminishing migration or displacement of an implant, comprising administering subepidermal by injection a volume of 1 to 10 ml of a viscoelastic medium through a 18 to 20 gauge needle by application of a pressure of about 15 N to about 40 N at a site of said human subject, wherein the viscoelastic medium comprises gel particles comprising cross-linked hyaluronic acid and derivatives thereof, wherein the concentration of said cross-linked hyaluronic acid and derivatives thereof in said gel particles, when subjected to a physiological salt solution, is in the range of from 12 to 23 mg/ml, and wherein at least 50% (v/v) of said gel particles has a size range, when subjected to the physiological salt solution, in the range of from 3 to 4 mm, wherein the hyaluronic acid is cross-linked with 1,4-butanediol diglycidyl ether, whereby migration or displacement of the gel particles from the administration site is prevented or decreased.

* * * * *